United States Patent
Chen et al.

(12)

(10) Patent No.: US 6,177,585 B1
(45) Date of Patent: Jan. 23, 2001

(54) BIMETALLIC PLATINUM CATALYSTS FOR HYDROSILATIONS

(75) Inventors: Wei Chen; Paul Charles Dinh; Ming-Shin Tzou, all of Midland, MI (US)

(73) Assignee: Dow Corning Corporation, Midland, MI (US)

( * ) Notice: Under 35 U.S.C. 154(b), the term of this patent shall be extended for 0 days.

(21) Appl. No.: 09/575,860

(22) Filed: May 19, 2000

(51) Int. Cl.$^7$ .................................................. C07F 7/04
(52) U.S. Cl. ............................................................. 556/479
(58) Field of Search ............................................... 556/479

(56) References Cited

U.S. PATENT DOCUMENTS

| | | | |
|---|---|---|---|
| 2,823,218 | 2/1958 | Speier et al. | 260/448.2 |
| 2,851,473 | 9/1958 | Wagner et al. | 260/448.2 |
| 3,220,972 | 11/1965 | Lamoreaux | 260/46.5 |
| 3,714,212 | * 1/1973 | Lengnick | 556/472 |
| 4,578,497 | 3/1986 | Onopchenko et al. | 556/479 |
| 5,347,027 | * 9/1994 | Ritscher et al. | 556/479 X |
| 5,561,231 | * 10/1996 | Dauth et al. | 556/472 |
| 5,637,548 | 6/1997 | Ito et al. | 502/330 |

FOREIGN PATENT DOCUMENTS

0533170A1   3/1993   (EP) .

* cited by examiner

*Primary Examiner*—Paul F. Shaver
(74) *Attorney, Agent, or Firm*—Melvin D. Fletcher

(57) ABSTRACT

A hydrosilation processing a silicon hydride with an unsaturated reactant in the presence of a supported bimetallic catalyst comprising an active hydrosilating metal such as platinum in elemental or compound form, and a surface segregating metal such as copper in elemental or compound form on a support.

26 Claims, No Drawings

BIMETALLIC PLATINUM CATALYSTS FOR HYDROSILATIONS

BACKGROUND OF THE INVENTION

The present invention is a hydrosilation process comprising contacting a silicon hydride with an unsaturated reactant in the presence of a supported bimetallic catalyst comprising an active hydrosilating metal such as platinum in elemental or compound form, and a surface segregating metal such as copper in elemental or compound form on a support.

It is known in the art to produce organosilicon compounds by reacting a silicon hydride containing compound with an unsaturated organic compound in the presence of a catalyst. This reaction is commonly referred to as hydrosilation or hydrosilylation. Typically the catalyst is monometallic platinum metal on a carbon support, a platinum compound generally in a solvent, or a platinum complex. The present invention uses a bimetallic catalyst such as platinum-copper, to increase the hydrosilation rate, total conversion product selectivity and increase process efficiency, while decreasing processing cost, compared to monometallic catalysts used for hydrosilations. Speier et al., U.S. Pat. No. 2,823,218, teaches a method for the production of organosilicon compounds by reacting Si—H with a compound containing aliphatic carbon atoms linked by multiple bonds in the presence of chloroplatinic acid. Lamoreaux, U.S. Pat. No. 3,220,972, teaches a similar process, however the catalyst is a reaction product of chloroplatinic acid.

Wagner et al., U.S. Pat. No. 2,851,473, disclose a process for the production of organosilicon compounds comprising reacting an unsaturated organic compound with a platinum-gamma alumina catalyst.

One of the major problems known in the art with hydrosilation reactions is the de-activation of the catalyst prior to the completion of the reaction. One method for reactivation of the catalyst has been to expose the reaction mixture to oxygen. For example, Onopchenko et al., U.S. Pat. No. 4,578,497, teaches the use of an oxygenated platinum containing catalyst for use in hydrosilating alkylsilanes. Kleyer et al., EP Patent Application No. 0533170A1, discloses a method for controlling a hydrosilation reaction by controlling the solution concentration of oxygen in the reaction mixture, relative to the platinum present in the reaction mixture.

SUMMARY OF INVENTION

The present invention is a hydrosilation process comprising contacting a silicon hydride with an unsaturated reactant in the presence of a supported bimetallic catalyst comprising an active hydrosilating metal such as platinum in elemental or compound form, and a surface segregating metal such as copper in elemental or compound form on a support.

DETAILED DESCRIPTION OF INVENTION

The present invention is a hydrosilation process comprising contacting a silicon hydride with an unsaturated reactant in the presence of a supported bimetallic catalyst comprising an active hydrosilating metal such as platinum in elemental or compound form, and a surface segregating metal such as copper in elemental or compound form on a support. The hydrosilation process comprises:

(A) contacting a silicon hydride described by formula $R^1_aH_bSiX_{4-a-b}$ where each $R^1$ is independently selected from the group consisting of alkyls comprising one to about 20 carbon atoms, cycloalkyls comprising about four to 12 carbon atoms, and aryls; each X is a halogen; a=0 to 3, b=1 to 3, and a+b=1 to 4; and (B) an unsaturated reactant selected from the group consisting of (i) substituted and unsubstituted unsaturated hydrocarbon compounds, (ii) silicon compounds comprising substituted or unsubstituted unsaturated hydrocarbon substituents, and (iii) mixtures of (i) and (ii);

in the presence of a supported bimetallic catalyst comprising an active hydrosilating metal in elemental or compound form and a surface segregating metal in elemental or compound form on a support, at a temperature of from about 0° C. to 350° C., the active hydrosilating metal being different from the surface segregating metal.

The contacting of the silicon hydride with the unsaturated reactant can be effected in standard reactors for conducting hydrosilation processes. The process may be run as a continuous, semi-continuous, or batch process.

Silicon hydrides useful in the present process are described by formula $R^1_aH_bSiX_{4-a-b}$ where each $R^1$ is independently selected from the group consisting of alkyls comprising one to about 20 carbon atoms, cycloalkyls comprising about four to 12 carbon atoms, and aryls; a=0 to 3, b=1 to 3, and a+b=1 to 4. $R^1$ can be a substituted or unsubstituted alkyl, cycloalkyl, or aryl as described. It is preferred that each $R^1$ be independently selected from the group consisting of alkyls comprising one to about six carbon atoms. Even more preferred is when each $R^1$ is methyl. Each X is a halogen and preferably X is chlorine. Examples, of silicon hydrides described by formula $R^1_aH_bSiX_{4-a-b}$ which may be useful in the present process include trimethylsilane, dimethylsilane, triethylsilane, dichlorosilane, trichlorosilane, methyldichlorosilane, dimethylchlorosilane, ethyldichlorosilane, cyclopentlydichlorosilane, methylphenylchlorosilane and (3,3,3-trifluoropropyl)dichlorosilane. Preferably, the silicon hydride is selected from a group consisting of dimethylchlorosilane, methyldichlorosilane, trichlorosilane and dichlorosilane.

The silicon hydride may contain siloxanes described by formula

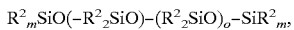

$$R^2_mSiO(-R^2_2SiO)-(R^2_2SiO)_o-SiR^2_m,$$

where $R^2$ independently selected from the group consisting of hydrogen, alkyls comprising one to about 20 carbon atoms, cycloalkyls comprising about four to 12 carbon atoms and aryls; m=0 to 3, n=0 to 100 and o=0 to 100. An example of a siloxane is bis-trimethylsiloxymethylhydridosilane.

The silicon hydride is contacted with an unsaturated reactant selected from the group consisting of (i) substituted and unsubstituted unsaturated hydrocarbon compounds, (ii) silicon compounds comprising substituted and unsubstituted unsaturated hydrocarbon substituents, and (iii) mixtures of (i) and (ii). For purpose of this invention, "unsaturated" means that the compound contains at least one carbon-carbon double bond or one carbon-carbon triple bond.

Specific examples of the unsaturated reactants useful in the process include unsubstituted cycloalkene compounds comprising at least four carbon atoms, substituted cycloalkene compounds comprising at least four carbon atoms, linear alkene compounds comprising two to about 30 carbon atoms, such as acetylene, ethylene, propene, butene, 1-octene, 1-dodecene, and 1-octadecene and branched alkene compounds comprising four to about 30 carbon atoms, such as isobutene, amylene, 2-methyl heptene and mixtures of two or more of any of the above.

The substituted and unsubstituted cycloalkene compounds useful in the process are those containing one or more unsaturated carbon-carbonbonds in the ring. The unsubstituted cycloalkene compounds may be, for example, cyclobutene, cyclopentene, cyclohexene, cycloheptene, cyclooctene, cyclopentadiene, 1,3-cyclohexadiene, and 1,3,5-cycloheptatriene. Substituted unsaturated compounds useful in the present invention may be, for example, 3-methylcyclopentene, 3-chlorocyclobutene, 4-phenylcyclohexene, and 3-methylcyclopentadiene. The preferred cycloalkene compounds are cyclohexene and cyclopentene, with cyclohexene being the most preferred.

Other unsaturated hydrocarbon compounds useful in the process are linear and branched alkene compounds including, for example, compounds with terminal unsaturation such as 1-hexene, 1,5-hexadiene, 1,4-hexadiene and compounds with internal unsaturation such as trans-2-hexene, 2-methyl-2-butene, 2,3-dimethyl-2-butene and unsaturated aryl containing compounds such as styrene and alpha-methylstyrene.

The unsaturated reactants may also comprise halogen, oxygen in the form of acids, anhydrides, esters, and ethers, and nitrogen. Two or more of the above described unsaturated hydrocarbon compounds may be used in the present process.

The unsaturated hydrocarbon compounds comprising halogen may include, for example, vinyl chloride, allyl chloride, allyl bromide, allyl iodide, methallyl chloride, 3,3,3-trifluoropropene, 4-chloromethyl styrene, chloroprene and 4-chlorostyrene.

Suitable unsaturated hydrocarbon compounds comprising oxygen can include, for example, ethers such as allyl and vinyl ethers; acids such as acrylic, methacrylic, vinylacetic, oleic, sorbic, and linolenic; and esters such as vinyl acetate, allyl acetate, butenyl acetate, allyl stearate, methylacrylate, ethylcrotonate, diallyl succinate and diallyl phthalate. Suitable nitrogen containing unsaturated hydrocarbon compounds include, for example, indigo, indole, acrylonitrile, and allyl cyanide.

Specifically included within the definition of unsaturated hydrocarbon compounds are those substituted by organo-functional moieties such as $CH_2=CHCH_2OC(O)C(CH_3)=CH_2$, $CH_2=CHCH_2NHCH_2CH_2NH_2$, $CH_2=CHCH_2NH_2$, $CH_2=CHCH_2OCH_2CHCH_2O$, $CH_2=CHCH_2SH$, $CH_2=CHSi\{O(CH_2)_2OCH_3\}_3$, $CH_2=CHCH_2N(HCl)HCH_2CH_2NHCH_2(C_6H_4)CH=CH_2$, and other similar compounds.

The unsaturated hydrocarbon compound can be a silicon compound comprising substituted and unsubstituted hydrocarbon substituents as described by, for example, formulas $(CH_2=CH(CH_2)_g)_h R^1_i Si(OR^1)_{4-h-i}$ and $(CH_2=CH(CH_2)_g)_h R^1_i SiX_{4-h-i}$, where $R^1$ and X are as previously described, g=0 to 12, h=1 to 3, i=0 to 3, and h+i=1 to 4. Suitable unsaturated hydrocarbon compounds are vinyltrimethoxysilane, vinyltriethoxysilane, methylvinyldimethoxysilane, hexenylmethyldimethoxysilane, methylvinyldichlorosilane and vinyltrichlorosilane.

Prior to contact of the silicon hydride with the unsaturated reactant, it may be preferable to treat or purify the unsaturated reactant. Methods useful for treating or purifying the unsaturated reactants are those known in the art for treating or purifying unsaturated organic compounds and include but are not limited to distillation and treatment with an adsorbent such as activated carbon, activated alumina or molecular sieves.

The relative amounts of silicon hydride and unsaturated reactant used in the present process can be varied within wide limits. Although one unsaturated carbon-carbon linkage per silicon bonded hydrogen atom is stoichiometric, there is no requirement that the process be run under stoichiometric conditions. Generally, it is preferred that the process be run with a stoichiometric excess of silicon hydride. Preferred is when the process is run with about 0.1 to 10 percent stoichiometric excess of silicon hydride.

The silicon hydride and unsaturated reactant are contacted in the presence of a supported bimetallic catalyst comprising an active hydrosilating metal and a surface segregating metal in elemental or compound form on a support, the active hydrosilating metal being different from the surface segregating metal. The active hydrosilating metal is selected from the group consisting of Group VIB and Group VIII metals in elemental or compound form. By the term "active hydrosilating" it is understood to mean use of a catalyst to react a silicon atom with an olefin. The active hydrosilating metal is selected from the group consisting of ruthenium, rhodium, cobalt, palladium, iridium, platinum, chromium and molybdenum metals in elemental or compound form.

Most preferably the active hydrosilating metal is ruthenium or platinum in elemental or compound form.

The surface segregating metal is selected from the group consisting of metals of Groups IB, IIB, IIIA, IIIB, IVA, IVB, VA, VB, VIB, VIIB, and VIII in elemental or compound form. By the term "surface segregating" it is meant that the metal having the lower heat of sublimation and larger atomic radius will segregate uniformly on the surface of the alloy as compared to non-uniform clumping. Preferably the surface segregating metal is selected from the group consisting of copper, nickel, tin, silver, zinc, cadmium, gold and ruthenium metals in elemental or compound form. Most preferably the surface segregating metal is copper or ruthenium in elemental or compound form.

Preferred bimetallic catalyst comprise an active hydrosilating metal selected from the group consisting of ruthenium, rhodium, cobalt, palladium, iridium, platinum, chromium and molybdenum in elemental or compound form and a surface segregating metals selected from the group consisting of copper, nickel, tin, silver, zinc, cadmium, gold, rhenium, palladium, cobalt, iron, osmium, iridium, and ruthenium metals in elemental or compound form on a support. More preferred is a bimetallic catalyst comprising an active hydrosilating metal selected from the group consisting of ruthenium, rhodium, cobalt, and platinum in elemental or compound form and a surface segregating metal selected from the group consisting of copper, nickel, tin, and gold in elemental or compound form on a support. Most preferred is a bimetallic catalyst comprising an active hydrosilating metal selected from the group consisting of ruthenium or platinum in elemental or compound form and copper as the surface segregating metal in elemental or compound form on a support.

The proportions and amounts of the active hydrosilating metal and the surface segregating metal in the bimetallic catalyst may vary. The active hydrosilating metal may comprise from 0.01 to about 20 percent by weight on an elemental basis of the catalyst and the surface segregating metal may comprise from 0.01 to about 20 percent by weight on an elemental basis of the catalyst. More preferably the active hydrosilating metal comprises from about 0.03 to 3 percent by weight of the catalyst and the surface segregating metal comprises from about 0.05 to 15 percent by weight of the catalyst on an elemental basis. Most preferably the active hydrosilating metal comprises from about 0.05 to 1 percent by weight of the catalyst and the surface segregating metal comprises from about 0.1 to 10 percent by weight of the catalyst on an elemental basis of the catalyst.

The particle size of the active hydrosilating and surface segregating metals dispersed on the support is in the range of 1 nm to about 500 nm. Preferably the particle size of the active hydrosilating and surface segregating metals dispersed on the support is in the range of about 5 nm to 60 nm. Most preferably particle size of the active hydrosilating and surface segregating metals dispersed on the support is in the range of about 10 nm to 20 nm.

The support for the bimetallic catalyst is selected from the group consisting of carbon, silica, titanium oxide, aluminum oxide, aluminosilicate and mixed oxides of aluminum oxide and zirconium oxide. Preferably the support is an activated carbon, and more specifically is activated carbon having a specific surface area in an unimpregnated condition of about 50 m$^2$/g to 1400 m$^2$/g.

Most preferably the support has a specific surface area of about 1100 m$^2$/g to 1300 m$^2$/g.

An example of a commercially available carbon which has been found to be well suited for use in various of the contemplated processes is a coal based carbon produced by Calgon Carbon Corporation under the designation "BPLF3", and may generally be characterized as having a specific surface area of 1100 m$^2$/g to 1300 m$^2$/g, a pore volume of 0.7 to 0.85 cm$^2$/g, and an averag pore radius of 12.3 to 14 angstroms. Based on an X-ray fluorescence analysis of this carbon, a typical bulk composition of the BPLF3 carbon has been determined to be as follows by weigh percent: silicon, 1.5 percent; aluminum, 1.4 percent; sulfur, 0.75 percent; iron, 0.48 percent; calcium,0.17 percent; potassium,0.086 percent; titanium,0.059 percent; magnesium,0.051 percent; chlorine,0.028 percent; phosphorus,0.026 percent; vanadium,0.010 percent; nickel, 0.036 percent; copper, 0.035 percent; chromium,0.028 percent; and manganese, 0.018 percent and the remainder being carbon.

The catalyst is preferably a supported bimetallic platinum/copper catalyst of from 0.01 to about 5 percent by weight of platinum calculated on an elemental basis on a carbon support having a specific surface area of at least about 200 m$^2$/g. More preferably, the catalyst includes from 0.10 to about 3 percent by weight of platinum and from 0.05 to about 5 percent by weight of copper, and the carbon support has a specific surface area of at least about 500 m$^2$/g. Most preferably, the catalyst includes from 0.1 to about 2 percent by weight of platinum and from 0.20 to about 2 percent by weight of copper, and the carbon support has a specific surface area of at least about 800 m$^2$/g.

Suitable platinum compounds for supporting on carbon are described, for example, in Onopchenko et al., U.S. Pat. No. 4,578,497; Lamoreaux, U.S. Pat. No. 3,220,972 and Speier, U.S. Pat. No. 2,823,218, all of which are hereby incorporated herein by reference. The platinum can be, for example, chloroplatinic acid, chloroplatinic acid hexahydrate, Karstedt's catalyst (i.e. a complex of chloroplatinic acid with sym-divinyltetramethyldisiloxane), dichlorobis(triphenylphosphine)-platinum(II), cis-dichlorobis(acetonitrile)-platinum(II), dicabonyldichloroplatinum(II), platinum chloride, and platinum oxide. A preferred platinum is selected from the group consisting of chloroplatinic acid, chloroplatinic acid hexahydrate, and platinum vinylsiloxane complexes such as a neutralized complexes of chloroplatinic acid with sym-divinyltetramethyldisiloxane. Suitable copper compounds for supporting on carbon are copper chloride, copper bromide, copper iodide, copper acetate and copper nitrate. Suitable ruthenium compounds for supporting on carbon are ruthenium chloride, ruthenium carbonyl, ruthenium acetylacetonate and hexaamineruthenium chloride.

The active hydrosilating metal and the surface segregating metal may be supported on the support using methods known in the art, such as wet impregnation or the in the present case, wet co-impregnation.

The contacting the silicon hydride and the unsaturated reactant in the presence of a supported bimetallic catalyst is conducted at a temperature within a range of about 0° C. to 350° C.

Preferably the temperature is within the range of about 60° C. to 250° C. Most preferably the temperature is within the range of about 80° C. to 190° C.

The catalyst may be premixed in a solvent for ease of handling. Suitable solvents include, for example, non-polar hydrocarbon solvents such as benzene, toluene, and xylene and polar solvents such as water, glycols and esters.

The following examples are provided to illustrate the present invention. These examples are not intended to limit the claims herein.

EXAMPLE 1

Evaluation of the hydrosilation of trichlorosilane with allyl chloride in the presence of 0.5% Pt–0.1% Cu/C bimetallic catalyst. An aqueous solution of chloroplatinic acid solution ($H_2PtCl_6 \cdot 6H_2O$, 0.52 gm, containing 38.6 wt % Pt) and $CuCl_2$ (0.875 gm) from Aldrich Chemical Company Inc., was prepared in deionized water (50 ml). The aqueous solution containing $H_2PtCl_6 \cdot 6H_2O$ and $CuCl_2$ was slowly added into this flask containing Calgon BPLF3 activated carbon (40 gm), 6×16 mesh, and the flask contents were agitated to evenly coat the activated carbon forming a bimetallic catalyst. The catalyst was pre reduced with a stream of hydrogen gas or a mixture of hydrogen-argon gas at a temperature range of 20° C. to 350° C. to convert the metallic salts to its metallic crystals prior to use. All experiments were conducted in a 1 liter continuous stirred-tank reactor (CSTR) equipped with a cooling coil, heating mantle, thermocouple and temperature controller. The CSTR was loaded with 20 gms of 0.5% Pt–0.1% Cu/C bimetallic catalyst and the catalyst was dried with argon gas at a flow rate of 2 liters/m at 140° C. for 4–6 hours. Trichlorosilane (330 gm/hr, 2.4 gmol/hr) and allyl chloride (150 gm/hr, 2.0gmol/hr) were fed into the CSTR and the temperature maintained at 20° C., at a pressure of 180 psig for a contact time of 2.5 mins. The product from the CSTR was analyzed by gas chromatography (GC) using a thermal conductivity detector (TCD) for product compositions. The example was repeated using the same procedure at various reaction temperatures. The reaction temperature, total conversion defined as the amount of allyl chloride reacted over the total contact time and reaction rate defined as the allyl chloride reacted per unit time per unit weight of catalyst are reported in Table 1.

EXAMPLE 2

Evaluation of the hydrosilation of trichlorosilane with allyl chloride in the presence of 0.5% Pt–0.5% Ru/C bimetallic catalyst prepared by a method similar to the method for preparing bimetallic catalyst described in example 1. The CSTR was loaded with 20 gms of 10 0.5% Pt–0.5% Ru/C bimetallic catalyst and the catalyst was dried with argon gas at a flow rate of 2 liters/m at 140° C. for 4–6 hours. Trichlorosilane (330 gm/hr, 2.4 gmol/hr) and allyl chloride (150 gm/hr, 2.0 gmol/hr) were fed into the CSTR and the temperature maintained at 40° C. at a pressure of 180 psig for a contact time of 2.5 mins. The product from the CSTR was analyzed by gas chromatography (GC) using a thermal conductivity detector (TCD) for product compositions. The experiment was repeated using the same procedure at various reaction temperatures. The reaction temperature, total conversion defined as the amount of allyl chloride reacted over the total contact time and reaction rate defined as the allyl chloride reacted per unit time per unit weight of catalyst are reported in Table 1.

EXAMPLE 3

Evaluation of the hydrosilation of trichlorosilane with allyl chloride in the presence of 0.5%-Pt/C catalyst prepared by a method similar to the method for preparing bimetallic catalyst described in example 1. The CSTR was loaded with 20 gms of 0.5%-Pt/C catalyst and the catalyst was dried with argon gas at a flow rate of 2 liters/m at 1 40° C. for 4–6 hours. Trichlorosilane (330 gm/hr, 2.4 gmol/hr) and allyl chloride (150 gm/hr, 2.0 gmol/hr) were fed into the CSTR and the temperature maintained at 40° C., at a pressure of 180 psig for a contact time of 2.5 mins. The product from the CSTR was analyzed by gas chromatography (GC) using a thermal conductivity detector (TCD) for product compositions. The experiment was repeated using the same procedure at various reaction temperatures. The reaction temperature, total conversion defined as the amount of allyl chloride reacted over the total contact time and reaction rate defined as the allyl chloride reacted per unit time per unit weight of catalyst are reported in Table 1.

TABLE 1

| Example No./ Catalyst | Reaction Temperature °C. | Reaction Rate gmol/hr/gm catalyst | Total Conversion % |
|---|---|---|---|
| Example 1 05%Pt-0.1%Cu/C | 20 | 0.04 | 55 |
|  | 80 | 0.06 | 82 |
|  | 120 | 0.06 | 87 |
| Example 2 0.5%Pt-0.5%Ru/C | 40 | 0.03 | 36 |
|  | 120 | 0.04 | 67 |
| Example 3 0.5%-Pt/C | 40 | 0.01 | 15 |
|  | 80 | 0.03 | 42 |
|  | 120 | 0.04 | 54 |

EXAMPLE 4

Evaluation of the hydrosilation of trichlorosilane with isobutene in the presence of 0.5% Pt–0.1% Cu/C bimetallic catalyst. The CSTR was loaded with 20 gms of 0.5% Pt–0.1% Cu/C bimetallic catalyst prepared by a method similar to the method for preparing bimetallic catalyst described in example 1. The catalyst was dried with argon gas at a flow rate of 2 liters/m at 140° C. for 4–6 hours. Trichlorosilane (380 gm/hr, 2.8 gmol/hr) and isobutene (150 gm/hr, 2.7 gmol/hr) were fed into the CSTR and the temperature maintained at 100° C., at a pressure of 180 psig. The product from the CSTR was analyzed by gas chromatography (GC) using a thermal conductivity detector (TCD) for product compositions. The experiment was repeated using the same procedure at various reaction temperatures. The reaction temperature, total conversion defined as the amount of isobutene reacted over the total contact time and reaction rate defined as the isobutene reacted per unit time per unit weight of catalyst are reported in Table 2.

EXAMPLE 5

Evaluation of the hydrosilation of trichlorosilane with isobutene in the presence of 0.5%-Pt/C catalyst. The CSTR was loaded with 20 gms of 0.5%-Pt/C catalyst prepared by a method similar to the method for preparing bimetallic catalyst described in example 1. The catalyst was dried with argon gas at a flow rate of 2 liters/m at 140° C. for 4–6 hours. Trichlorosilane (380 gm/hr, 2.8 gmol/hr) and isobutene (150 gm/hr, 2.7 gmol/hr) were fed into the CSTR and the temperature maintained at 100° C., at a pressure of 180 psig. The product from the CSTR was analyzed by gas chromatography (GC) using a thermal conductivity detector (TCD) for product compositions. The experiment was repeated using the same procedure at various reaction temperatures. The reaction temperature, total conversion defined as the amount of isobutene reacted over the total contact time and reaction rate defined as the isobutene reacted per unit time per unit weight of catalyst are reported in Table 2.

TABLE 2

| Example No. Catalyst | Reaction Temperature °C. | Reaction Rate gmol/hr/gm catalyst | Total Conversion % |
|---|---|---|---|
| Example 4 0.5%-Pt-0.1%Cu/C | 100 | 0.015 | 32 |
| Example 5 0.5%-Pt/C | 100 | 0.0005 | 3 |
|  | 140 | 0.002 | 6 |

EXAMPLE 6

Evaluation of the hydrosilation of trichlorosilane with isobutene in the presence of 0.5% Pt–0.1% Cu/C bimetallic catalyst in a continuous fixed-bed reactor (FBR). A tubular reactor 1 inch diameter by 48 inch long equipped with a cooling, heating oil bath, thermocouple and temperature controller was loaded with 165.5 gms of 0.5% Pt–0.1% Cu/C bimetallic catalyst prepared by a method similar to the method for preparing bimetallic catalyst described in example 1. The catalyst was dried with argon gas at a flow rate of 2 liters/m at 140° C. for 8 hours. Trichlorosilane (380 gm/hr, 2.8 gmol/hr) and isobutylene (150 gm/hr, 2.7 gmol/hr) were fed into the FBR and the reactor jacket temperature maintained as described in Table 3. The product from the FBR was analyzed by gas chromatography (GC) using a thermal conductivity detector (TCD) for product compositions. The experiment was repeated using the same procedure at various reaction temperatures. The reaction temperature, total conversion defined as the amount of isobutene reacted over the total contact time are reported in Table 3.

TABLE 3

| Reactor Jacket Temperature °C. | Total Conversion % |
|---|---|
| 75 | 52 |
| 90 | 70 |
| 110 | 78 |
| 135 | 90 |

EXAMPLE 7

Evaluation of the hydrosilation of methyldichlorosilane with 3,3,3-trifluoropropene in the presence of 0.5% Pt–0.1% Cu/C bimetallic catalyst. A CSTR was loaded with 50.5 gms of 0.5% Pt–0.1% Cu/C bimetallic catalyst prepared by a method similar to the method for preparing bimetallic catalyst described in example 1. The catalyst was dried with argon gas at a flow rate of 2 liters/m at 140° C. for 4–6 hours. Methyldichlorosilane (330 gm/hr, 2.4 gmol/hr) and 3,3,3-trifluoropropene (270 gm/hr, 3.4 gmol/hr) were fed into the CSTR and the temperature maintained at 40° C., at a pressure of 300 psig for a contact time of 5 mins. The product from the CSTR was analyzed by gas chromatography (GC) using a thermal conductivity detector (TCD) for 3,3,3-trifluoropropylmethyldichlorosilane, and 1-(methyl)-2,2,2-trifluoroethylmethyldichlorosilane (isomer adduct) compositions. The experiment was repeated using the same procedure at various reaction temperatures. The reaction temperature, percent of 3,3,3-trifluoropropylmethyldichlorosilane and 1-(methyl)-2,2,2-trifluoroethylmethyldichlorosilane defined as the isomer adduct, total conversion defined as the amount of 3,3,3-trifluoropropene reacted over the total contact time and the reaction rate defined as the amount of 3,3,3-trifluoropropene reacted per unit time per unit weight of catalyst are reported in Table 4.

EXAMPLE 8

Evaluation of the hydrosilation of methyldichlorosilane with 3,3,3-trifluoropropene in the presence of 0.5% Pt/C catalyst. A CSTR was loaded with 50.5 gms of 0.5% Pt/C catalyst. The catalyst was dried with argon gas at a flow rate of 2 liters/m at 1 40° C. for 4–6 hours. Methyldichlorosilane (330 gm/hr, 2.4 gmol/hr) and 3,3,3-trifluoropropene(270 gm/hr, 3.4 gmol/hr) were fed into the CSTR and the temperature maintained at 60° C., at a pressure of 300 psig for a contact time of 5 mins. The product from the CSTR was analyzed by gas chromatography (GC) using a thermal conductivity detector (TCD) for 3,3,3-trifluoropropylmethyldichlorosilane,and 1-(methyl)-2,2,2-trifluoroethylmethyldichlorosilane (isomer adduct) compositions. The experiment was repeated using the same procedure at various reaction temperatures. The reaction temperature, percent of 3,3,3-trifluoropropylmethyldichlorosilane and 1-(methyl)-2,2,2-trifluoroethylmethyldichlorosilane defined as isomer adduct, total conversion defined as the amount of 3,3,3-trifluoropropene reacted over the total contact time and the reaction rate defined as the amount of 3,3,3-trifluoropropene reacted per unit time per unit weight of catalyst are reported in Table 4.

ous reaction temperatures. The reaction temperature, contact time, total conversion defined as the amount of 1-octene reacted over the total contact time and reaction rate defined as the 1-octene reacted per unit time per unit weight of catalyst are reported in Table 5.

EXAMPLE 10

Evaluation of the hydrosilation of trichlorosilane with 1-octene in the presence of 0.5%-Pt/C catalist. The CSTR was loaded with 41.3 gms of 0.5%-Pt/C catalyst prepared by a method similar to the method for preparing bimetallic catalyst described in example 1. The catalyst was dried with argon gas at a flow rate of 2 liters/m at 140° C. for 4–6 hours. Tricholorosilane (330 gm/hr, 2.4 gmol/hr) and 1-octene (330 gm/hr, 2.9 gmol/hr) were fed into the CSTR and the temperature maintained at 80° C., at a pressure of 180 psig. The product from the CSTR was analyzed by gas chromatography (GC) using a thermal conductivity detector (TCD) for octyltrichlorosilane. The experiment was repeated using the same procedure at various reaction temperatures. The reaction temperature, contact time, total conversion defined as the amount of 1-octene reacted over the total contact time and reaction rate defined as the 1-octene reacted per unit time pre unit weight of catalyst are reported in Table 5

TABLE 4

| Example No. Catalyst | Reaction Temperature ° C. | Reaction Rate gmol/hr/gm catalyst | Total Conversion % | 3,3,3-F$_3$PrSiMeCl$_2$ % | Isomer Adduct % |
|---|---|---|---|---|---|
| Example 7 0.5%-Pt- 0.1% Cu/C | 40 | 0.016 | 27 | 100 | Not Detected |
| | 80 | 0.039 | 70 | 100 | Not Detected |
| | 100 | 0.049 | 75 | 100 | Not Detected |
| Example 8 0.5%-Pt/C | 60 | 0.010 | 18 | 100 | Not Detected |
| | 100 | 0.027 | 49 | 100 | Not Detected |

EXAMPLE 9

Evaluation of the hydrosilation of trichlorosilane with 1-octene in the presence of 0.5% Pt–0.1% Cu/C bimetallic catalyst. The CSTR was loaded with 41.3 gms of 5 0.5% Pt–0.1% Cu/C bimetallic catalyst. The catalyst was dried with argon gas at a flow rate of 2 liters/m at 140° C. for 4–6 hours. Trichlorosilane (330 gm/hr, 2.4 gmol/hr) and 1-octene (330 gm/hr, 2.9 gmol/hr) were fed into the CSTR and the temperature maintained at 80° C., at a pressure of 180 psig for a contact time of 3.7 mins. The product from the CSTR was analyzed by gas chromatography (GC) using a thermal conductivity detector (TCD) for product compositions. The experiment was repeated using the same procedure at vari-

TABLE 5

| Example No. Catalyst | Reaction Temperature ° C. | Contact Time min. | Reaction Rate gmol/hr/gm cat. | Total Conversion % |
|---|---|---|---|---|
| Example 9 0.5% Pt-0.1 Cu/C | 80 | 3.5 | 0.049 | 83 |
| | 80 | 3.5 | 0.048 | 85 |
| | 120 | 3 | 0.066 | 85 |
| Example 10 0.5% Pt/C | 80 | 3.8 | 0.048 | 66 |
| | 80 | 3.8 | 0.059 | 67 |
| | 120 | 3.8 | 0.047 | 84 |

EXAMPLE 11

Evaluation of the hydrosilation of trichlorosilane with allyl chloride in the presence of 0.5% Pt–0.1% Cu/C bimetallic catalyst in a continuous fixed-bed reactor (FBR). A tubular reactor 1.6 inch diameter by 48 inch long equipped with a cooling and heating oil bath, thermocouple and temperature controller was loaded with 463.5 gms of 0.5%

Pt–0.1% Cu/C bimetallic catalyst prepared by a method similar to the method for preparing bimetallic catalyst described in example 1. The catalyst was dried with argon gas at a flow rate of 2 liters/m at 140° C. for 8 hours. Trichlorosilane (5360 gm/hr, 39.55 gmol/hr) and allyl chloride (2620 gm/hr, 34.24 gmol/hr) were fed into the FBR and the reactor wall temperature maintained as described in Table 6. The product from the FBR was analyzed by gas chromatography (GC) using a thermal conductivity detector (TCD) for product compositions. The experiment was repeated using the same procedure at various feed rates. The reaction temperature, and total conversion defined as the amount of allyl chloride reacted over the total contact time are reported in Table 6.

TABLE 6

| Example No. Catalyst | HSiCl$_3$ Feed Rate, gm/hr | AllylCl Feed Rate, gm/hr | Reactor Jacket Temp. ° C. | Contact Time min. | Total Conversion % |
| --- | --- | --- | --- | --- | --- |
| Example 11 0.5% Pt- 0.1 Cu/C | 5360 2610 | 2620 1310 | 60 53 | 3.5 7.1 | 92 93 |

EXAMPLE 12

Evaluation of the hydrosilation of trichlorosilane with allyl chloride in the presence of 0.5% Pt–0.5% Sn/Al$_2$O$_3$ bimetallic catalyst. The CSTR was loaded with 20 gms of 0.5% Pt–0.5% Sn/Al$_2$O$_3$ bimetallic catalyst and the catalyst was dried with argon gas at a flow rate of 2 liters/m at 140° C. for 4–6 hours. Trichlorosilane (330 gm/hr, 2.4 gmol/hr) and allyl chloride (150 gm/hr, 2.0 gmol/hr) were fed into the CSTR and the temperature maintained at 120° C. at a pressure of 180 psig for a contact time of 2.5 mins. The product from the CSTR was analyzed by gas chromatography (GC) using a thermal conductivity detector (TCD) for product compositions. Total conversion defined as the amount of allyl chloride reacted over the total contact time was 26%.

EXAMPLE 13

Evaluation of the hydrosilation of trichlorosilane with allyl chloride in the presence of 0.5% Pt–0.5% Re/Al$_2$O$_3$ bimetallic catalyst. The CSTR was loaded with 20 gms of 0.5% Pt–0.5% Re/Al$_2$O$_3$ bimetallic catalyst and the catalyst was dried with argon gas at a flow rate of 2 liters/m at 140° C. for 4–6 hours. Trichlorosilane (330 gn/hr, 2.4 gmol/hr) and allyl chloride (150 gm/hr, 2.0 gmol/hr) were fed into the CSTR and the temperature maintained at 120° C. at a pressure of 180 psig for a contact time of 2.5 mins. The product from the CSTR was analyzed by gas chromatography (GC) using a thermal conductivity detector (TCD) for product compositions. Total conversion defined as the amount of allyl chloride reacted over the total contact time was 73%.

EXAMPLE 14

Evaluation of the hydrosilation of bis-trimethylsiloxymethylhydridosilane with 1-octene in the presence of 0.5% Pt–0.1% Cu/C bimetallic catalyst. The CSTR was loaded with 48.2 gms of 0.5% Pt–0.1% Cu/C bimetallic catalyst and the catalyst was dried with argon gas at a flow rate of 2 liters/m at 140° C. for 4–6 hours. Bis-trimehtylsiloxymethylhydridosilane described by formula Me$_3$SiOSiMe(H)OSiMe$_3$ (264 gm/hr) and 1-octene (126 gm/hr) were fed into the CSTR and the temperature maintained at 100° C. at a pressure of 160 psig for a contact time of 7.4 mins. The product from the CSTR was analyzed by gas chromatography (GC) using a thermal conductivity detector (TCD) for product compositions. Total conversion defined as the amount of 1-octene reacted over the total contact time was 21%.

We claim:
1. A hydrosilation process comprising:
 (A) contacting a silicon hydride described by formula R$^1_a$H$_b$SiX$_{4-a-b}$ where each R$^1$ is independently selected from the group consisting of alkyls comprising one to about 20 carbon atoms, cycloalkyls comprising about four to 12 carbon atoms, and aryls; each X is a halogen; a=0 to 3, b=1 to 3, and a+b=1 to 4; and
 (B) an unsaturated reactant selected from the group consisting of
  (i) substituted and unsubstituted unsaturated hydrocarbon compounds,
  (ii) silicon compounds comprising substituted or unsubstituted unsaturated hydrocarbon substituents, and
  (iii) mixtures of (i) and (ii);
in the presence of a supported bimetallic catalyst comprising an active hydrosilating metal in elemental or compound form and a surface segregating metal in elemental or compound form on a support at a temperature range of about 0° C. to 350° C., the active hydrosilating metal being different from the surface segregating metal.
2. A process according to claim 1, wherein the silicon hydride is selected from a group consisting of methyldichlorosilane, trichlorosilane, dimethylchlorosilane, dichlorosilane and trimethylsilane.
3. A process according to claim 1, wherein the unsaturated reactant is selected from the group consisting of isobutene, 1-octene, allyl chloride, acetylene, ethylene, propylene, 1-hexene, 1-dodecene, 1-octadecene, 1,5-hexadiene, 1,4-hexadiene, cyclopentene, cyclohexene, cyclooctene and 3,3,3-trifluoropropene.
4. A process according to claim 1, wherein the active hydrosilating metal is selected from the group consisting of ruthenium, rhodium, cobalt, palladium, iridium, platinum, chromium and molybdenum metals in elemental or compound form and the surface segregating metal is selected from the group consisting of copper, nickel, tin, silver, zinc, cadmium, gold, rhenium, osmium, iridium and ruthenium metals in elemental or compound form.
5. A process according to claim 1, wherein the active hydrosilating metal is ruthenium or platinum in elemental or compound form and the surface segregating metal is copper, tin or ruthenium in elemental or compound form.
6. A process according to claim 1, wherein the active hydrosilating metal comprises from 0.01 to about 20 percent by weight on an elemental basis of the catalyst and the surface segregating metal comprises from 0.01 to about 20 percent by weight on an elemental basis of the catalyst.
7. A process according to claim 1, wherein the active hydrosilating metal comprises from 0.03 to about 3 percent by weight of the catalyst and the surface segregating metal comprises from 0.05 to about 15 percent by weight of the catalyst on an elemental basis.
8. A process according to claim 1, wherein the active hydrosilating metal comprises from 0.05 to 1 percent by weight of the catalyst and the surface segregating metal comprises from 0.1 to about 10 percent by weight of the catalyst on an elemental basis of the catalyst.

9. A process according to claim 1, wherein the process is conducted with stoichiometric excess of silicon hydride in relation to the unsaturated carbon—carbon bonds of the unsaturated reactant.

10. A process according to claim 1, wherein the process is conducted with 0.1 to about 10 percent stoichiometric excess of silicon hydride in relation to the unsaturated carbon—carbon bonds of the unsaturated reactant.

11. A process according to claim 1, wherein the particle size of the active hydrosilating and surface segregating metals dispersed on the support is in the range of 1 nm to about 500 nm.

12. A process according to claim 1, wherein the particle size of the active hydrosilating and surface segregating metals dispersed on the support is in the range of about 5 nm to 60 nm.

13. A process according to claim 1, wherein the particle size of the active hydrosilating and surface segregating metals dispersed on the support is in the range of about 10 nm to 20 nm.

14. A process according to claim 1, wherein support is selected from the group consisting of carbon, silica, titanium oxide, aluminum oxide, aluminosilicate, and mixed oxides of aluminum oxide and zirconium oxide.

15. A process according to claim 1, wherein the support is an activated carbon.

16. A process according to claim 15, wherein the activated carbon has a specific surface area of about 50 $m^2/g$ to 1400 $m^2/g$.

17. A process according to claim 15, wherein the activated carbon has a specific surface area of about 1100 $m^2/g$ to 1300 $m^2/g$.

18. A process according to claim 1, wherein the contacting is at a temperature range of about 60° C. to 250° C.

19. A process according to claim 1, wherein the contacting is at a temperature in the range of about 80° C. to 190° C.

20. A hydrosilation process comprising:
(A) contacting a silicon hydride described by formula $R^1{}_aH_bSiX_{4-a-b}$ where each $R^1$ is independently selected from the group consisting of alkyls comprising one to about 20 carbon atoms, cycloalkyls comprising about four to 12 carbon atoms, and aryls; each X is a halogen; a=0 to 3, b=1 to 3, and a+b=1 to 4; and
(B) an unsaturated reactant selected from the group consisting of
  (i) substituted and unsubstituted unsaturated hydrocarbon compounds,
  (ii) silicon compounds comprising substituted or unsubstituted unsaturated hydrocarbon substituents, and
  (iii) mixtures of (i) and (ii);
in the presence of a supported bimetallic catalyst comprising an active hydrosilating metal comprising platinum elemental or compound form and a surface segregating metal comprising copper, ruthenium, tin, or rhenium in elemental or compound form on a carbon support at a temperature range of about 80° C. to 190° C., the active hydrosilating metal being different from the surface segregating metal.

21. A process according to claim 20, wherein the silicon hydride is selected from a group consisting of methyldichlorosilane, trichlorosilane, dimethylchlorosilane and dichlorosilane and the unsaturated reactant is selected from the group consisting of isobutene, 1-octene, allyl chloride and 3,3,3-trifluoropropene.

22. A hydrosilation process comprising:
(A) contacting a silicon hydride described by formula $R^1{}_aH_bSiX_{4-a-b}$ where each $R^1$ is independently selected from the group consisting of alkyls comprising one to about 20 carbon atoms, cycloalkyls comprising about four to 12 carbon atoms, and aryls; each X is a halogen; a=0 to 3, b=1 to 3, and a+b=1 to 4; and a siloxanes described by formula

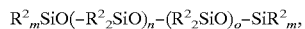

where $R^2$ independently selected from the group consisting of hydrogen, alkyls comprising one to about 20 carbon atoms, cycloalkyls comprising about four to 12 carbon atoms and aryls; m=0 to 3, n=0 to 100 and o=0 to 100, and
(B) an unsaturated reactant selected from the group consisting of
  (i) substituted and unsubstituted unsaturated hydrocarbon compounds,
  (ii) silicon compounds comprising substituted or unsubstituted unsaturated hydrocarbon substituents, and
  (iii) mixtures of (i) and (ii);
in the presence of a supported bimetallic catalyst comprising an active hydrosilating metal in elemental or compound form and a surface segregating metal in elemental or compound form on a support at a temperature range of about 0° C. to 350° C., the active hydrosilating metal being different from the surface segregating metal.

23. A process according to claim 22, wherein the siloxane is bis-trimethylsiloxymethylhydridosilane.

24. A process according to claim 22, wherein the silicon hydride is selected from a group consisting of methylidicholorosilane, trichlorsilane, dimethylchlorosilane, dichlorosilane and trimethylsilane.

25. A process according to claim 22, wherein the unsaturated reactant is selected from the group consisting of isobutene, 1-otene, allyl chloride, acetylene, ethylene, propylene, 1-hexene, 1-dodecene, 1-octadecene 1,5-hexadiene, cyclopentene, cyclohexene, cyclooctene and 3,3,3-trifluoropropene.

26. A process according to claim 22, wherein the active hydrosilating metal is selected from the group consisting of ruthenium, rhodium, cobalt, palladium, iridium, platinum, chromium and molybdenum meterals in elemental or compound from and the surface segregating metal is selected from the ground consisting of copper, nickel, tin, silver, zinc, cadmium, gold, rhenium, osmium, iridium and ruthenium metals in elemental or compound form.

* * * * *